United States Patent
Causevic et al.

(10) Patent No.: US 6,974,421 B1
(45) Date of Patent: Dec. 13, 2005

(54) HANDHELD AUDIOMETRIC DEVICE AND METHOD OF TESTING HEARING

(75) Inventors: Elvir Causevic, Jefferson County, MO (US); Eldar Causevic, Jefferson County, MO (US)

(73) Assignee: Everest Biomedical Instruments Co., St. Louis, MO (US)

( * ) Notice: Subject to any disclaimer, the term of this patent is extended or adjusted under 35 U.S.C. 154(b) by 0 days.

(21) Appl. No.: 10/019,451

(22) PCT Filed: Apr. 28, 2000

(86) PCT No.: PCT/US00/11389

§ 371 (c)(1),
(2), (4) Date: Jul. 30, 2002

(87) PCT Pub. No.: WO00/65983

PCT Pub. Date: Nov. 9, 2000

Related U.S. Application Data

(60) Provisional application No. 60/131,542, filed on Apr. 29, 1999.

(51) Int. Cl.[7] .............................................. A61B 5/00
(52) U.S. Cl. .................................................... 600/561
(58) Field of Search ............................... 600/559, 561; 73/585; 128/898; 702/57; 381/23.1, 60

(56) References Cited

U.S. PATENT DOCUMENTS

| | | |
|---|---|---|
| 3,396,673 A | 8/1968 | Livelsberger et al. |
| 4,284,847 A * | 8/1981 | Besserman .................. 73/585 |
| 5,197,332 A | 3/1993 | Shennib |
| 5,267,571 A | 12/1993 | Zurek et al. |
| 5,601,091 A | 2/1997 | Dolphin |
| 5,738,633 A | 4/1998 | Christiansen |
| 5,868,682 A | 2/1999 | Combs et al. |
| 5,885,225 A | 3/1999 | Keefe et al. |
| 5,916,174 A | 6/1999 | Dolphin |
| 6,110,126 A * | 8/2000 | Zoth et al. .................. 600/559 |
| 6,366,863 B1 * | 4/2002 | Bye et al. ..................... 702/57 |

FOREIGN PATENT DOCUMENTS

| | | |
|---|---|---|
| DE | 4234782 | 4/1994 |
| WO | 9843566 | 10/1998 |

\* cited by examiner

*Primary Examiner*—Max F. Hindenburg
*Assistant Examiner*—Brian Szmal
(74) *Attorney, Agent, or Firm*—Polster, Lieder, Woodruff & Lucchesi, L.C.

(57) ABSTRACT

Handheld apparatus (100), and method for comprehensive hearing testing with pass/refer results applicable for large scale neonatal screening, adult screening, full hearing diagnostic is disclosed. The apparatus (100) contains a signal processor (1), integral ear probe (150), and remote ear, and scalp probes (104) all packaged as a single handheld battery operated device (100). The apparatus (100) preferably performs a battery of tests, either independently or combined: oto-acoustic measurements utilizing a novel digital signal processing method for evoked oto-acoustic signal processing, auditory brain stem response test, tympanometry, and oto-reflectance. Algorithms for automatic test sequence, and pass/refer indication for the tests are provided.

24 Claims, 5 Drawing Sheets

HANDHELD AUDIOMETRIC DEVICE AND METHOD OF TESTING HEARING

This application claims of U.S. Provisional Ser. No. 60/131,542, filed Apr. 29, 1999.

TECHNICAL FIELD

This invention relates to the field of auditory measurement devices and associated screening methods. In particular, the invention relates to a hand-held auditory measurement device, which has features beneficial to all neonatal screening programs. While the invention is described with particular emphasis to its auditory screening application, those skilled in the art will recognize the wider applicability of the inventive principles disclosed hereinafter.

BACKGROUND ART

Universal neonatal auditory screening programs have expanded greatly because of improved auditory measurement capability, improved rehabilitation strategies, increased awareness of the dramatic benefits of early intervention for hearing impaired babies and changes in governmental policies. Current neonatal auditory screening approaches, however, do not account adequately for the many different types and degrees of auditory abnormalities that are encountered with present screening approaches. Because of this, individual screening tests based on a single measurement can be influenced negatively by interaction among various independent auditory abnormalities. Current screening approaches have not considered adequately the entire screening program including (i) physical characteristics of the measurement device i.e., portability, physical size and ease of use, (ii) operational characteristics of the device i.e., battery life, amount of record storage, required operating training, etc. and/or (iii) program logistics i.e., retesting mechanisms, referral mechanisms record processing, patient tracking, report writing, and other practical aspects. These factors can interact negatively to increase the total cost of an auditory screening program including the primary economic cost of screening, testing, the secondary economic cost of additional testing, and non-economic costs such as parental anxiety incurred when provided with incorrect information.

These costs, both actual and human, can be reduced by reducing the cost per test, reducing the false positive rate, and resolving false positive screening results at the bedside prior to hospital, discharge. The cost per screening can be reduced with a dedicated device optimized for screening in any location and enhanced to allow effective operation by minimally trained personnel. The performance characteristic of the device of our invention includes reduced measurement time, the ability to operate and configure without an external computer, the ability to integrate and interpret all test results, the ability to store large number of test results, long battery life, and bi-directional wireless transfer of data to and from external devices.

We have found false positive results can be reduced in two ways. First, the initial screening test performance can be improved with enhanced signal processing, more efficient test parameters, and by combining different types of tests. Second, false positive rates also can be reduced by providing a mechanism for resolving an initial screening test failure at the bedside at the time of the initial screening. This capability is provided through the availability of an automated screening auditory brainstem response (ABR) test capability provided by the same device. Secondly, operational processes of a screening program can be improved through the use of several onboard computer based expert systems. These computer based expert systems provide improved automatic interpretation of single test results, automatic interpretation of multiple test results, and improved referral processes through the matching of local referral sources with various test outcomes, such as a referral to a specific type of follow-up, whether it be a pediatrician, audiologist, otolaryngologist, or a nurse. The device disclosed hereinafter integrates in a single, hand-held device, a single stimulus transducer, a single processor and a single software application for otoacoustic emission (OAE). ABR testing, tympanometry and otoreflectance, as well as OAE simulator.

An auditory abnormality is not a single, clearly defined entity with a single cause, a single referral source and a single intervention strategy. The peripheral auditory system has three separate divisions, the external ear, the middle ear, and the sensorineural portion consisting of the inner ear or cochlea and the eight cranial nerve. Abnormalities can and do exist independently in all three divisions and these individual abnormalities require different intervention and treatment. Prior art physical and operational characteristics of devices and their influences on program logistics can interact negatively to increase the total cost of an auditory screening program. The primary economic cost is the cost of each screening test though this is not the only economic cost. A screening test failure is called a "refer" and usually is resolved with an expensive full diagnostic test scheduled several weeks after hospital discharge, resulting in significant economic cost. A substantial portion of these costs is unnecessary if the screening false positive rate is high. Non economic costs include parental anxiety for false positive screening results, unfavorable professional perception of program effectiveness for programs with high false positive rates and even inappropriate professional intervention because of misleading screening results.

The intervention of multiple measurements into a single hand-held instrument allows for very important new functionality not available with existing neonatal auditory screening devices. This functionality includes (1) detection of common external and middle ear abnormalities; (2) the detection of less common sensorineural hearing loss associated with outer hair cell abnormalities, and (3) the detection of even less common sensorineural hearing loss associated with inner hair cell or auditory nerve abnormality. Moreover, the device disclosed hereinafter has the potential to improve the accuracy and reliability of OAE measurements, to allow for optimal interpretation of both the OAE and ABR results, and to improve the referral process.

Attempts have been made in the past to provide the capabilities provided by the present invention. In particular. U.S. Pat. Nos. 5,601,091 ('091) and 5,916,174 ('174) disclose audio screening apparatus which purport to provide a hand-held portable screening device. However, the screening device disclosed in those patents is used in conjunction with a conventional computer, and requires a docking station for full applicational use. In no way does the disclosure of either patent provide a hand-held device that can be used independently of any other computer. That is to say, the invention disclosed hereinafter provides a device of significantly reduced size i.e. hand-held, which is capable of providing OAE and ABR testing, as well as tympanometry otoreflectance, and OAE simulator. It can be operated in a stand-alone mode, independently of any other computer connection, if desired. The device includes a patient database, with names, and full graphic display capability. The device also preferably is provided with a wireless infrared and an RS 232 connection port to provide output directly to printers or to a larger database where such is required.

The '174 and '091 patents also operate on a linear averaging method to remove background noise. While such method works well for its intended purposes, use of a linear averaging method is time consuming. Consequently, we developed a frame overlap method for rejecting noise and improving signal reliability in a device which measures, in the embodiment illustrated, 7¼"×3 ¾"×1½".

SUMMARY OF INVENTION

One of the objects of this invention is to provide a reduced size hand-held device for auditory screening which provides OAE, ABR, tympanometry, otoreflectance and OAE simulator operation.

Another object of this invention is to provide an audio screening device, which is hand-held and operates in a fully stand-alone mode, operating independently of any other computer connection.

Another object of this invention is to provide a hand-held device that provides a patient database on the device.

Another objection of this invention is to provide a hand-held audio screening apparatus that provides for full graphic display on the device itself.

Another object of this invention is to provide a device that increases noise rejection and reduces processing time through the use of frame overlapping techniques.

A further object of this invention is to provide a device with ABR testing that automates electrode impedance checking prior to test.

Another object of this invention is to provide a device which is low in cost, and which can be adapted to provide a wide ranging of auditory screening applications.

In accordance with this invention, generally stated, an effective auditory screening method and device are provided. The integration of an OAE screening device and ABR screening device into a single, hand-held instrument enables a user to detect less common sensorineural hearing loss associated with outer hair cell abnormalities and the detection of less common sensor hearing loss associated with inner hair cell abnormalities. In the preferred embodiment, the device includes a portable hand-held enclosure containing a digital signal processor. The processor has a computer program associated with it, capable of conducting both otoacoustic emission test procedures and auditory brainstem response test procedures for a test subject. A display device is mounted to the enclosure, and displays patient information, test setup procedure, and test results including graphing of test results. The enclosure includes a connection point for a probe, the connection point being operatively connected to the signal processor. The device also includes an onboard power supply, making the device completely self contained.

A method of testing OAE response in a test subject is provided which utilize a unique method of noise reduction to provide acceptable data even in high level ambient noise conditions of the test subject's environment.

BEST MODE FOR CARRYING OUT THE INVENTION

The following detailed description illustrates the invention by way of example and not by way of limitation. This description will clearly enable one skilled in the art to make and use the invention, and describes several embodiments, adaptations, variations, alternatives and uses of the invention, including what we presently believe is the best mode for carrying out the invention. It will nevertheless be understood that no limitation in the scope of the invention is thereby intended, and that alterations and further modifications of the illustrative devices is contemplated, including but not limited to further applications of the principles of the invention illustrated herein as would normally occur to one skilled in the art to which this invention relates.

Figures 1, 2, 3:
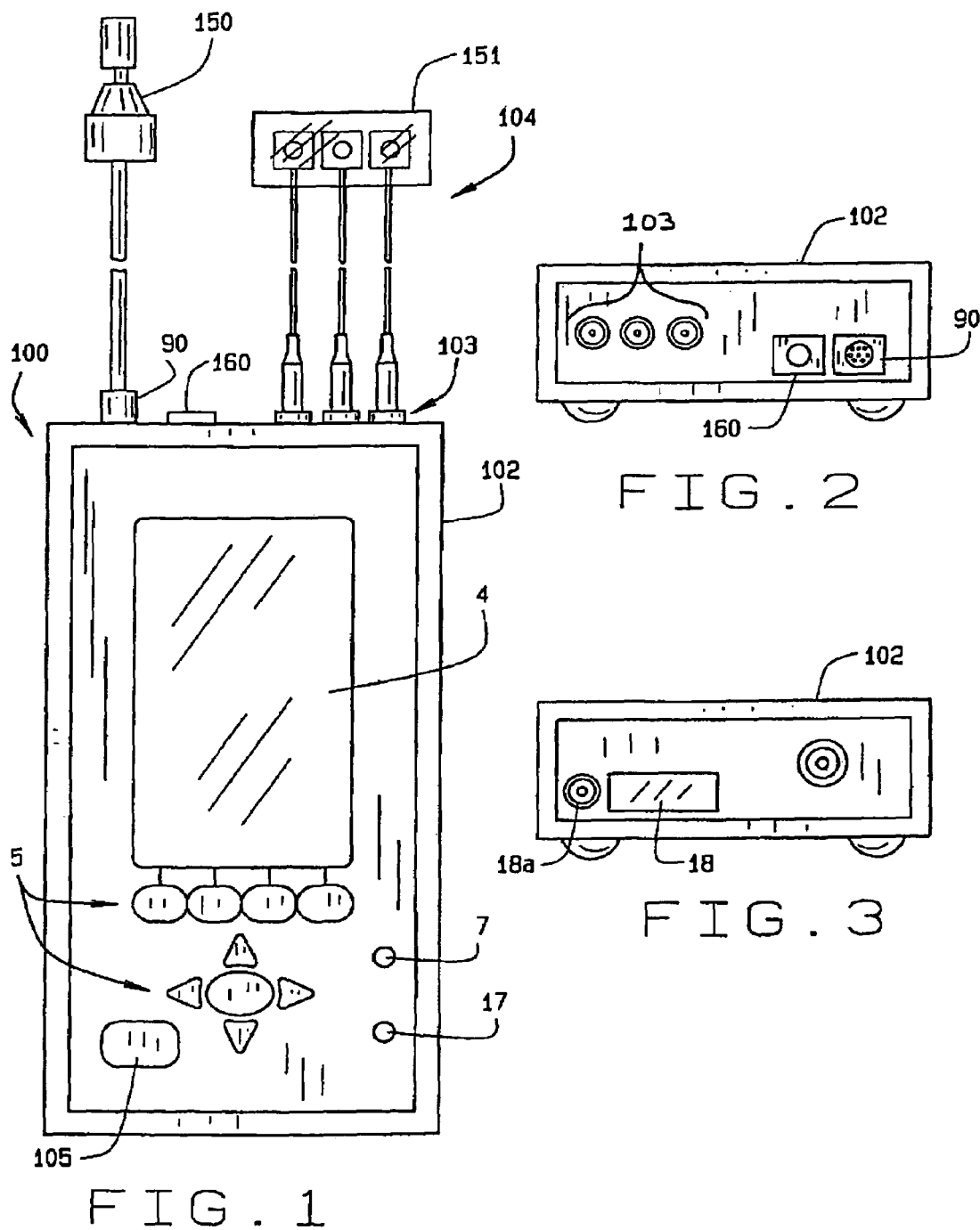
FIG. 1 is a top plan view of one illustrative embodiment of audio screen device of the present invention.
FIG. 2 is a view in end elevation.
FIG. 3 is a view in end elevation of the end opposite to that shown in FIG. 2

Referring now to FIGS. 1–3, reference numeral 100 illustrates one embodiment of the audio screening device of the present invention. The screening device 100 includes an enclosure 102, which in the preferred embodiment, and for purposes of illustration and not for limitation, measures 7¼" long by 3¾" wide by 1½" deep. It is important to note that the device 100 can be carried by the user without compromise, and truly represents a portable hand-held device having full functionality as described below. The device 100 includes a keyboard 5, an LCD display 4, an LED pass/refer indicator 7, and an LED AC charging indicator 17. Again, by way of illustration and not by limitation, it should be noted that the screen 4 measures, in the preferred embodiment, approximately 2" by 3⅜". The measurement is not necessarily important, except to show that the LCD display is fully functional for a user, and the unit can operate independently of any other computer system. In the embodiment illustrated, the enclosure 102 also houses an infrared port 18, a compatible RS-232 port 18a, a probe connection 90 for an ear probe 150, and an interface 103 for a plurality of electrodes 104. The electrodes 104 are shown attached to a conventional carrier 151.

Ear probe 150 is conventional and is not described in detail. Suitable probes are commercially available from Etymotic Research, Part No. ER-10C, for example.

A novel feature of this invention is the provision of an OAE simulator ear probe interface 160. The simulator function permits a user to test the integrity of the entire OAE test system, by providing active feedback and simulation of a test subject's ear.

Figure 4:
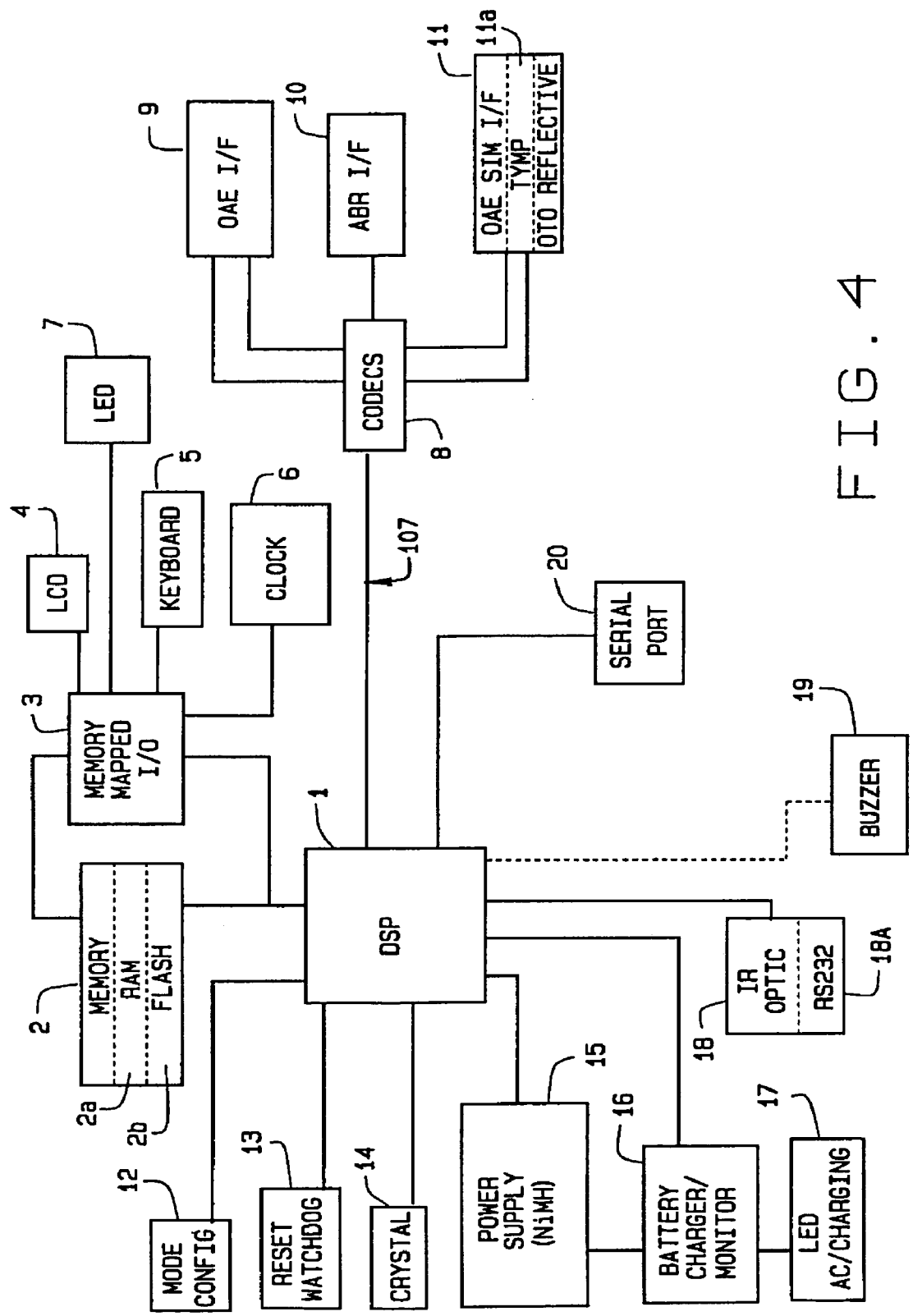
FIG. 4 is a block diagrammatic view of the device shown in FIG. 1.

Referring now to FIG. 4, a block diagram view of the device 100 is shown and described. The device 100 contains OAE, ABR and OAE simulator capabilities in a single, hand-held package. Preferably, the system shown in FIG. 4 is manufactured on a single printed circuit board, with mixed signal design for both analog and digital operation. The device preferably is low powered, and generally operates at 3.3 volts, except for the LCD 4 and some low power portions of the analog circuitry employed with the device 100.

A digital signal processor 1 is the control for the device 100. In the preferred embodiment illustrated, the processor 1 is a Motorola chip DSP 56303. All signal processing functions described hereinafter are performed by the processor 1, as well as the control of all input and output functions of the device 100. In addition, the graphic functions, user interface, patient data storage functions and other device functionality are controlled by the processor 1. In conventional design logic, the digital signal processor 1 is used for signal processing, and a separate micro controller is used for device control. We have been able to eliminate the separate microprocessor, resulting in substantial savings in space, cost and power consumption.

A memory subsystem 2 is operatively connected to the processor 1. The memory subsystem 2 includes a random access memory 2a for storing intermediate results and holding temporary variably an a flash memory 2b for storing non-volatile, electrically programmable variables, patient data and configuration information. In the embodiment illustrated, the flash memory 2b is substantially oversized, enable the device 100 to accommodate as many as 300 full patient records, as well as multiple configurations files.

A memory mapped input/output device 3 is operatively connected to the memory subsystem 2 and to the digital signal processor 1. The memory mapped input/output 3 in turn is operatively connected to the LCD display 4, the keyboard 5, the pass/referral LED indicator 7 and a real time clock 6.

The LCD display 4 is the largest non-custom LCD available. While custom LCD displays can be obtained, they add prohibitive cost to the product. The LCD display 4 provides the user with 128×256 pixels of graphics. That display is sufficient to present full waveforms of audiometric tests conducted by the device 100. The keyboard 5 preferably is a membrane switch keyboard, which incorporates only the minimum keys necessary for operation of the device 100. All keys are programmable, except for the on/off key 105.

A real time clock 6 is operatively connected to the processor 1 through the memory mapped device 3. The clock 6 enables the processor 1 to provide a time stamp for each patient and test performed, as well as providing time signals for internal operation of the device 100.

The LED pass/refer diode 7 is used to convey test results to non-trained users, namely a nurse as opposed to an audiologist or otolaryngologist. Use of the LED 7 avoids confusion or misinterpretation of the LCD graphics display 4, and allows use of the device 100 in low light areas, where the LCD display 4 may be difficult to interpret.

The plurality of analog to digital/digital to analog coder/decoders 8 (codecs 8) is operatively connected to the signal processor 1. As will be appreciated by those skilled in the art, the codecs 8 are special integrated circuit chips that perform analog to digital and digital to analog conversion. The codecs 8 are operatively connected to the signal processor 1 along a dedicated serial link indicated by the reference numeral 107. The codecs 8 in turn are operatively associated with a plurality of input/output devices, which provide the functionality of the device 100 under control of the processor 1.

An otoacoustic emission interface 9 is operatively connected to the signal processor 1 through the associated codecs 8. The interface 9 preferably is a low noise, differential analog circuit with high common mode noise rejection. The interface 9 is intended to drive two sound transducers inserted in the ear canal which produce a variety of signals, from pure tones at various frequencies to chirps, clicks, sine waveforms etc. The otoacoustic emission interface 9 can present tones at all standard audiometric frequencies and sound pressure levels. The device employed with the interface 9 includes a microphone, also inserted in the ear canal, which collects signals coming back from the ear, and provides sufficient linear amplification to present the signals to the codecs 8. In various embodiments of this invention, the interface 9 also can be used for otoreflectance measurements for assessing some middle ear conditions.

The ARB interface 10 consists of a plurality of analog signal processing chips, not shown individually, which filter and amplify the signals connected from the scalp of a subject via electrode wires 104. In this mode of operation, the ear is presented with a repeated auditory stimulus, which causes firing of the eighth nerve, and the associated nerve, pass Into the brainstem. As those firings occur, electrical potentials are generated all the way to the scalp, and there they are detected by the electrodes 104. An additional function of the interface 10 is to provide automated impedance check of the placement of electrodes. Once the electrodes are in place, a small current is, injected through the electrodes into the scalp of the subject, and the impedance between electrodes is measured. Impedance can be varied by placement of the electrodes. Once the impedance is within a predetermined range for operation, ABR signal connection can begin. It is important to note that impedance checking can be accomplished without unplugging the electrodes. That is to say checking is automatic. As later described in greater detail, the measured ABR response is based on the detection of a peak in the waveform in a point approximately up to 15 milliseconds after a sound click, depending upon gestational age or patient age. The actual latency of this peak is then compared to the latency of this peak in normal hearing neonates or adults.

The otoacoustic emission simulator interface 11 is used to check the integrity of the OAE system. It includes a transducer or speaker and a microphone. The microphone collects the signals presented by the OAE probe, presents them to the codecs 8 and processor 1 for signal processing, and then the speaker presents the corresponding tone at the correct frequency and amplitude back to the original OAE probe thus providing an active, calibrated test cavity.

Our invention optionally may include a tympanometry interface 11a in place of the interface 11. The tympanometry interface 11a comprises an electronic output channel to drive a miniature pump, not shown, which can produce pressure or a vacuum in the ear canal of a test subject. A corresponding pressure sensor is used to measure this pressure, and the signal from the pressure sensor is fed into an analog input of the codecs 8. The signal can be used as an independent feature, and the device will show full graphics output on the LCD 4 in real time. In the alternative, this test may be used in combination with the OAE or ABR test to compensate for middle ear conditions.

A mode configuration system 12, a reset watchdog system 13, a crystal clock 14, a power supply 15 and a battery charger 16 all are also positioned within the enclosure 102 and operatively connected to the processor 1. While each of these blocks is required for operation of the device 102, they are standard in nature and are not described in detail.

The processor 1 has an input output channel 18, which are preferably an infrared connection and an isolated RS-232 interface. The device 100 can communicate with any infrared compatible or RS-232 compatible personal computer, printer, or other digital device for data transmission. Data transmission may include patient information, configuration data for the signal processor 1, or software program updates.

A buzzer 19 also is provided. The buzzer 19 provides an audio feedback to the user for keyboard actions and audio indication for error conditions.

A serial port 20 also is operative connected to the processor 1. The serial port 20 is utilized to provide direct programming of the processor 1 from a personal computer, for example, and is intended for use only for initial software download and major software program upgrades of the processor 1.

A distortion product otoacoustic emission (DPOAE) is a tone generated by a normal ear in response to the application of two external tones. When two tones, $f_1$ and $f_2$ are applied to an ear, the normal non-linear outer hair cells generate a third tone $f_{dp}$, which is called a distortion product. $F_{dp}$ then propagates from the outer hair cells back to the ear canal where it is emitted. The level of the DPOAE can be used as a measure of outer hair cell function. If the outer hair cell system is absent or otherwise not functioning properly, the non-linearity will be absent or reduced and the $f_{dp}$ will either not be generated or generated at a lower than expected level.

The measured DPOAE is highly dependent upon the specific tones that invoke it. The frequencies of $f_1$ and $f_2$, and their respective levels in the ear canal, L1 and L2 must be controlled precisely. Under known signal conditions, the largest distortion product is generated at a very specific frequency ($f_{dp}=2\ f_1-f_2$), and level $L_{dp}$. Comparison of the level of $L_{dp}$ with known values from individuals with normal outer hair cell systems forms the basis of the decision of whether the patient either passed the screening (pass/refer LED 7) or requires a referral for a more complete diagnostic testing.

Signals other than pure tones can be presented to the ear, which will also evoke a response from the ear, such as clicks, chirps, etc. DPOAE is used to as an example, the other stimuli would be processed the same way.

The processor 1 utilizes a unique method of detecting signals for the OAE test. While the method is a time domain sum and average operation, the key concept is to reuse data from adjacent frames to average with the current frame. This method is described for the purpose of this specification as "sliding". The limit to the size of the overlap is the auto correlation of original data. The method works on the assumption that the data within the overlap frames is different, and that the noise is uncorrelated. It is key to keep the frame size an integer number (one or more) of the original data cycles.

The important difference between the method of the present invention and linear averaging is that the overlapping number M (sum operation) equals ((frame number divided by (frame size minus 1)) times (frame size divided by (frame data cycle length plus 1))) which is larger than the received data frame number by a factor by which the previous frame is slid. Therefore, the expected performance of this method is better than standard linear averaging. In this method, the frame size divided by frame data cycle length must be an integer. The method is shown diagrammatically in FIG. 5 and FIG. 6.

Figure 7:
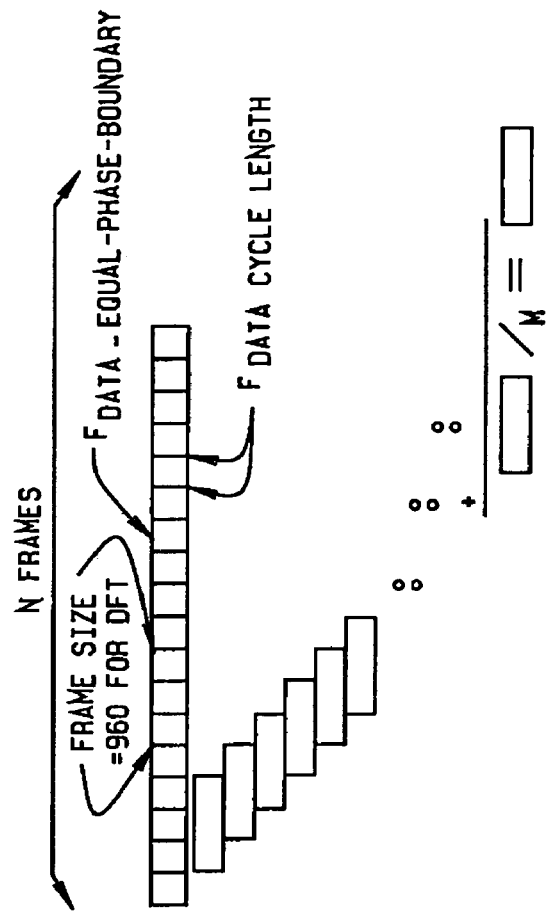
FIG. 7 is a diagrammatic view of frame sliding implemented by the algorithm of FIG. 4.
Figure 8:
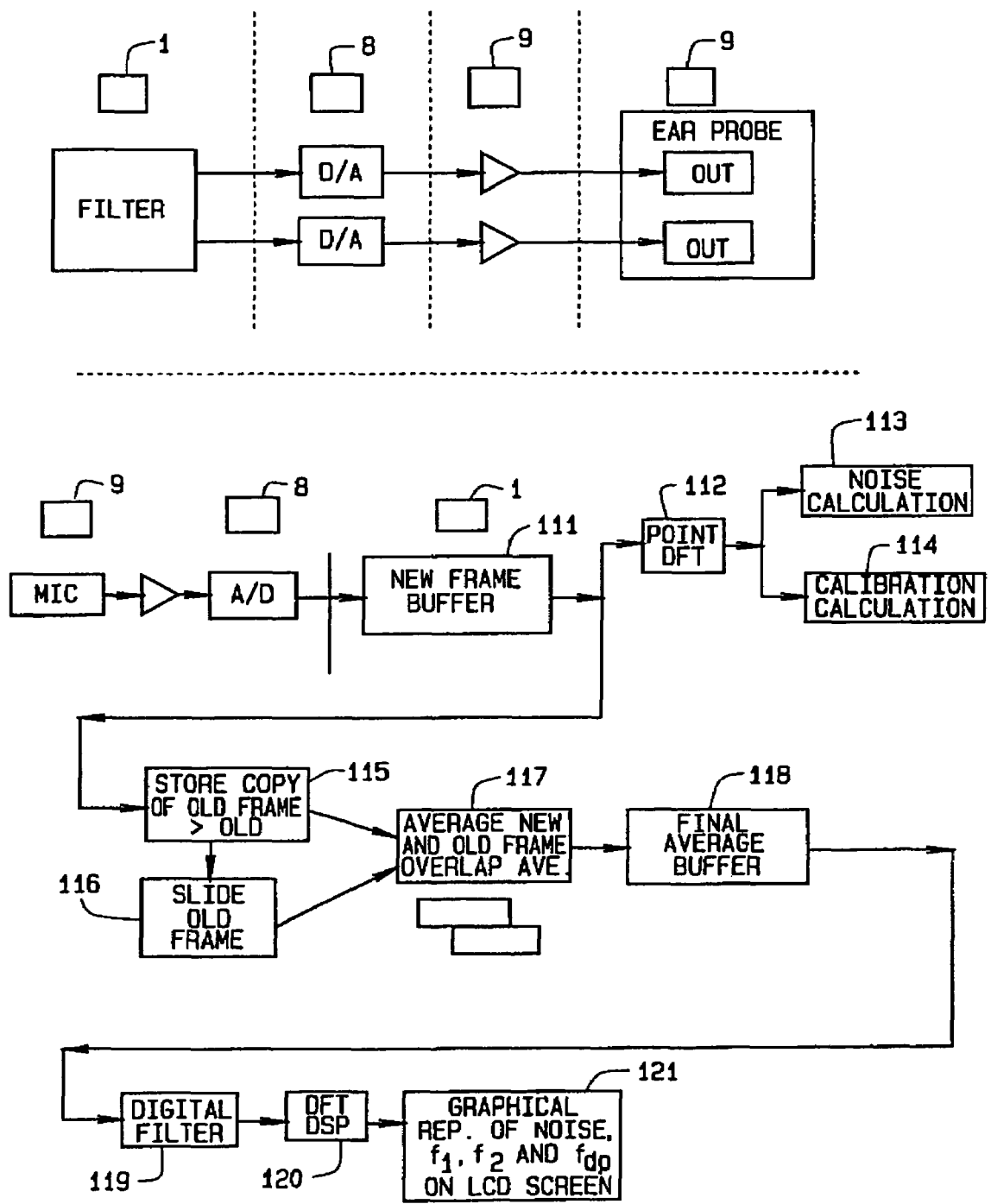
FIG. 8 is a block diagrammatic view of the algorithm implemented with respect to OAE testing to improve the signal to noise ratio employed with the device of FIG. 1.

The processor 1 algorithm is implemented and explained with reference to FIG. 7 and FIG. 8. As there shown, the processor 1 sends an output through, the digital analog converter portion of the codecs 8 through the OAE interface 9 to the ear probe, utilized in conjunction with the device 100. The ear probe includes a microphone which returns signals through the interface 9 and the codecs 8 to a new frame buffer 111 in the processor 1. The size of the new frame buffer 111 is calculated to be an integer number of samples of the two primary tones at frequencies f1 and f2, and also, an integer number of samples of the otoacoustic tone produced by the ear at $f_{dp}$. This is a critical step to assure quality of subsequent signal processing, by avoiding windowing techniques, which can introduce substantial artifacts. Tables of numbers for each standard frequency employed in the device 100 and for other frequencies in use or intended for use in the device 100 are available, and are programmed into the algorithm once the user selects the test frequencies. Should a combination of frequencies by required for which no common integer number can be found to fit in a practical size frame, the frame size is adjusted to $f_{dp}$ and the frame is windowed prior to Fourier Transformation, but this method is used only in extreme cases since in normal operation, the required frequencies are available.

The data from the single frame is passed to a point Discrete Fourier Transform 112 (DFT) block which calculates the signal's magnitude and phase content, but only at frequencies of interest, including $f_1$, $f_2$, $f_{dp}$ to determine a noise floor. Windowing is induced prior to DFT to reduce edge effects, although windowing induces energy at other bands. The block 112 is used only for temporary calculations, and the windowed data is not reused again. The output of block 112 is the magnitude and phase of primary signals at $f_1$ and $f_2$ and the noise floor figure of time at $f_{dp}$. The output of block 112 forms an input to frame rejection block 113 and to an on-line calibration calculation block 114.

With the information on the magnitudes at various frequencies, a noise calculation algorithm is employed at and around $f_{dp}$ to determine the noise floor. The magnitude of the noise floor and frequency content are used against a set of predetermined conditions i.e. a comparison against an empirically derived table contained in the processor 1, to determine the outcome of the frame. That outcome has three distinct possibilities. First, if the noise magnitude and frame content exceed a multi-threshold condition at measured frequency bands, the new frame is rejected. Second, if the noise magnitudes fall between a set of reject thresholds and a set of accept thresholds, the data in the frame is disregarded, but the noise information is kept to update the noise level average.

Third, if the noise magnitudes are below the accept thresholds, the frame is kept and passed on for further processing and the noise magnitudes are averaged together with the noise average of the previous frame. This information is used to update thresholds, such that the system adapts to environmental conditions.

When the information about magnitudes of primary tones at $f_1$ and $f_2$, and the noise floor information at and around $f_{dp}$, an online calibration of the level of magnitudes takes place. Several actions occur in the calibration block 114. First, if the noise floor is large when no primary tones are present, the frequency of the primaries is adjusted within predetermined limits. A new $f_{dp}$ is calculated, and the noise content of frequency bins at and around $f_{dp}$ is checked again. This process is repeated until a stable, low noise floor is established. No primary tones are played through the speaker through this process. Once the primaries are presented, they are stepped up to the full output amplitude, as programmed by the user and calibrated in the ear by increasing the output of the codecs 8. No data collection from the ear has taken place yet. At this time, if the level is not reached in a user predetermined time, and at the rate of increase of the primaries, the test is aborted due to lack of fit or the low quality of fit of the probe in the ear canal. Once the proper fit is achieved, and testing begins, data collection takes place. During the entire process of data collection, the levels of tones at $f_1$ and $f_2$ are checked to ensure that they remain within predetermined limits throughout the test. If they exceed those limits, the output is adjusted up or down to compensate until a maximum compensation limit is reached, at which time, the test is aborted and the user is notified. Also, the magnitude at and around $f_{dp}$ is continuously monitored to assure low noise floor, and if necessary, the frequency of the primary tones are adjusted on-line within predetermined limits to avoid the high external noise region. The change in frequencies of the primaries is minimal, and within the specified tolerances of the device 100, and have been shown not to affect the magnitude of the tone within the ear at $f_{dp}$.

The block 115 is a store/copy buffer. As a frame is collected in new frame buffer 111, a copy of it is saved for processing of the subsequent frames.

The buffer 115 receives frame data from new frame buffer 111. The store and copy frame buffer 115 has a variable depth, depending the number of frames averaged together. Buffer 115 provides an output to a block 116 and a block 17. The block 116 operates with the stored previous frames, which are slid by a predetermined amount and the empty spaces padded with zeros for subsequent processing in the averaging old and new frame block 117.

In block 117, the frames are averaged together to reduce the uncorrelated noise present. Theoretically, the noise is reduced by a factor of one over the square root of the number of averaged frames. The frames are averaged in a linear fashion, sample by sample and a new frame is created at the end of the averaging operation. The advantage of this method is that the data is essentially correlated against a slid copy of itself, slid far enough away to avoid averaging the same information content. This provides either a substantial reduction in uncorrelated noise energy for the same amount of sampling time or a substantial reduction in sampling time to obtain the equivalent noise reduction when compared to standard linear averaging.

The minimum limit to the sliding of the data, and to the reuse of old data frame is the autocorrelation function of the data in the frame, which can be predetermined or calculated on-line. This method is equivalent to taking much smaller frames and averaging them together. However, for the purposes of the subsequent Fourier Transformations and filtering taking place, the frame size is required to be large (i.e., 960 samples at 48 kilohertz sampling rate), to obtain several full cycles of each of the tones at f1, f2 and $f_{dp}$. The problem with taking a large number of very small frames is that the Fourier Transforms or other signal processing methods require several cycles of data for proper operation. The method of the present invention outperforms standard linear averaging of large frames because of the reduction in time as well as providing proper operation of the Fourier Transforms.

The block 118 obtains the averaged data from the block 117, and collects it in a buffer that is used for subsequent processing and signal statistics. The output of the block 118 is digitally filtered in the block 119. The filter 119 removes any remaining high or low frequency components not required for final data presentation.

The averaged and filtered data is converted to frequency domain, in the embodiment illustrated, by using a discrete Fourier Transform in the block 120, and the data then is ready for presentation in block 121. As will be appreciated by those skilled in the art, other signal processing methods are available to convert data, and those other methods are compatible with the device 100.

As indicated above, the device 100 enables the LCD 4 to present information to a user graphically in real time on the device itself, complemented with textual and numeric information about the quality of the fit, amplitudes, frequency, noise floors and other related information.

Figure 5:
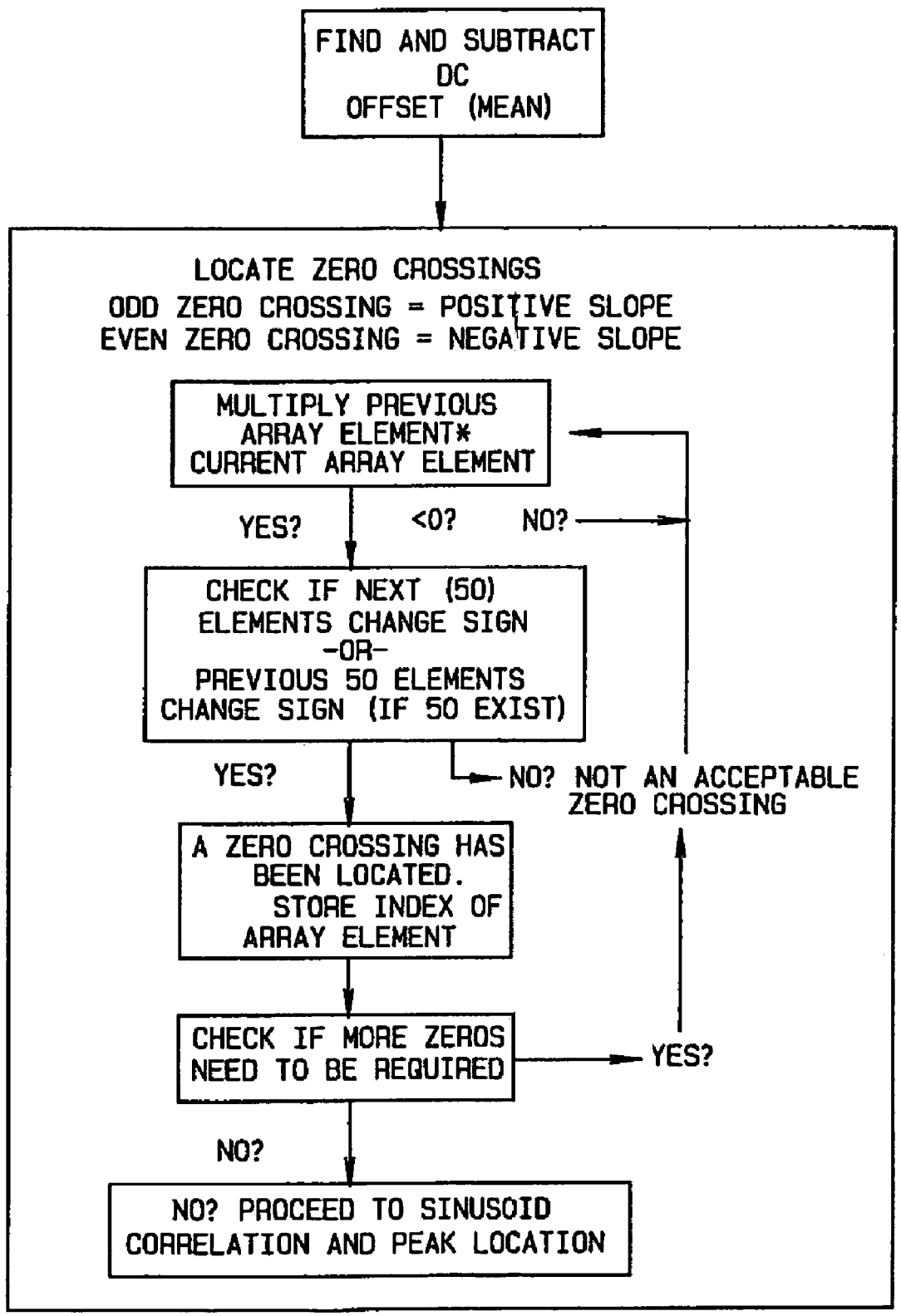
FIGS. 5 and 6 are block diagrammatic views of the algorithm employed with the device of FIG. 1 in connection with ABR testing.
Figure 6:
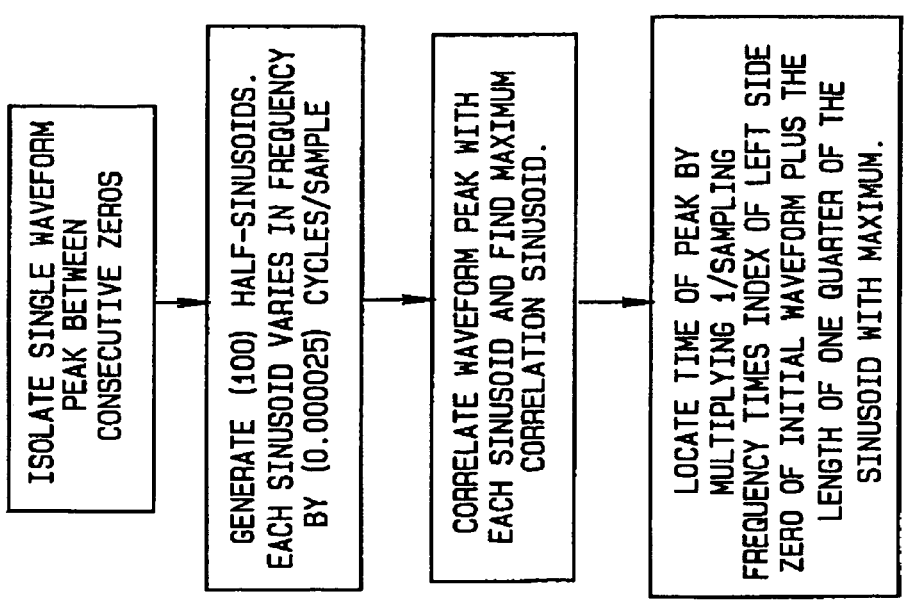

Operation of the device for ABR testing is shown in FIG. 5 and FIG. 6. In ABR testing, the magnitude of the fifth peak is the one that is of primary interest, and the device 100 determines the magnitude of the fifth peak by counting zero crossings, after substantial filtering and digital preprocessing. As shown in FIG. 5 and FIG. 6, the system proceeds to count zero crossings and stores an index of an array element upon determination of a zero crossing. If additional zero crossings are required, the procedure is, repeated until the fifth peak is determined. Upon detection, the single waveform is isolated, and the waveform peak is correlated to find the maximum correlation sinusoid. Thereafter, the device 100 determines the time of occurrence of the fifth peak and that value is checked against empirical data to obtain proper correlation.

Numerous variations, within the scope of the appended claims, will be apparent to those skilled in the art in light of the foregoing description and accompanying drawings. For example, the design of the enclosure may vary in other embodiments of the invention. Likewise, LCD display 4 may be replaced with other display devices. As indicated in the specification, we use a discrete Fourier Transform to obtain data for display. Other signal processing methods are compatible with the broader aspects of the invention. These variations are merely illustrative.

What is claimed is:

1. An auditory screening device, comprising:
a portable hand-held enclosure;
a signal processor housed by said enclosure, said signal processor configured with a computer program operated on command by a user to produce one or more auditory tests and associated stimulus signals selected from a group comprising otoacoustic auditory emission test procedures, auditory brainstem response test procedures, tympanometry, and otoreflectance for a test subject;
a memory module housed by said hand-held enclosure, said memory module operatively connected to said signal processor and configured to maintain at least one test subject record;
a display device mounted to said enclosure, said display device being operatively connected to said signal processor for displaying results of a selected auditory test in real time;
a probe connection point on said enclosure, said probe connection point being operatively connected to said signal processor;
a power supply; and
wherein said signal processor is configured to perform a time domain sum and average over time for detecting otoacoustic auditory emission signals using an offset frame overlap method.

2. An auditory screening device, comprising:
a portable hand-held enclosure;
a signal processor housed by said enclosure, said signal processor having a computer program operated on command by a user, said program configured to produce auditory tests selected from a group comprising otoacoustic emission test procedures, auditory brainstem response test procedures, tympanometry, otoreflectance, and combinations thereof for a test subject;

a display device mounted to said enclosure, said display device being operatively connected to said signal processor, said display device displaying the results of the selected test in real time;

a probe connection point on said enclosure, said probe connection point being operatively connected to said signal processor; and a power supply for operating the signal processor;

wherein said signal processor is configured to perform a time domain sum and average over time for otoacoustic emission test signal detection, using a frame overlap method; and wherein said auditory screening device further comprises a memory subsystem that includes provisions for patient data.

3. The device of claim 2 wherein an auditory brainstem test signal is determined by digital signal processing and counting zero crossings of correlated internally generated sinusoids.

4. A method of conducting an otoacoustic auditory emission audio test, comprising the steps of:

inserting a probe in a patient's ear, said probe including a speaker and a microphone;

connecting said probe to a hand-held device;

generating an auditory signal in said hand-held device, detecting incoming auditory signals generated in said ear via said microphone;

converting said incoming auditory signals to digital signal data;

storing said incoming digital signal data in a new frame buffer;

sizing said new frame buffer to be an integer number of samples of two primary tones at frequencies $f_1$ and $f_2$ and an integer number of samples of a tone produced by said ear at frequency $f_{dp}$;

passing digital signal data from a single frame to a discrete Fourier transform process to calculate a frequency specific magnitude and phase content of said incoming auditory signal signal;

comparing said calculated magnitude and phase to a table to determine whether to reject the digital signal data, to discard the digital signal data but update a noise table; or to save the digital signal data;

collecting said digital signal data until a predetermined number of frames have been saved;

averaging said digital signal data over a predetermined number of sequential frames, wherein data from sequentially preceding frames is slid by a predetermined number of data points prior to said averaging;

converting said averaged data to a frequency domain; and displaying said averaged frequency domain data to the user in a hand-held device in real time.

5. The method of claim 4 further including the step of saving the digital signal data internally in said hand-held device.

6. The method of claim 5 further including the step of sending to the user an indication of the subject passing or failing the test.

7. The method of claim 4 further including the step of transferring said digital signal data from said hand-held device to an external unit.

8. An auditory screening device comprising:
a hand-held enclosure;
a signal processor within said enclosure;
a memory module within said enclosure operatively connected to said signal processor;

a display screen mounted to said enclosure, said display screen being operatively connected to said signal processor;

a computer program at least partial contained in said signal processor, said computer program being accessible by a user to perform an otoacoustic emission test and an auditory brainstem response test for a test subject, said memory module maintaining a plurality of test subject records for display on said display screen; and wherein the otoacoustic auditory emission information is recorded by frames, and information from a preceding frame is used in connection with information of a succeeding frame to reduce the signal to noise level in the received signals.

9. The device of claim 8 wherein the amount of information employed with a succeeding frame is obtained from the formula:

$$M = \left(\frac{f_n}{f_s - 1}\right) \times \left(\frac{f_s}{f_{dcl} + 1}\right)$$

where M equals overlap number, $f_n$ equals frame number, $f_s$ equals frame size and $f_{dd}$ equals frame data cycle length.

10. The device of claim 9 wherein said computer program further includes tympanometry test procedures conducted independently or in conjunction with otoacoustic auditory emission and auditory brainstem response tests.

11. The device of claim 10 wherein the computer program determines data information for the brainstem response test by counting zero crossings of a sinusoid.

12. A method of conducting an auditory test in which a reduced noise ratio is obtained by:

receiving auditory signal information in frames;

making a determination to accept a frame, reject a frame and update a noise average, or to discard a frame based upon at least one predefined parameter; and averaging data in a current accepted frame with data from at least one previous accepted frame, wherein said data from said at least one previous accepted frame is slid by a predetermined number of data points.

13. A method of conducting an otoacoustic auditory emission test in which reduced noise ratio is obtained by:

receiving otoacoustic auditory emission signal information in frames;

overlapping information from a proceeding frame for use in connection with information from a succeeding frame;

making a determination to accept the data, to reject the data but update a noise average, or to discard the data based upon predefined parameters;

wherein an overlap is determined from the formula:

$$M = \left(\frac{f_n}{f_s - 1}\right) \times \left(\frac{f_s}{f_{dcl} + 1}\right)$$

where M equals overlap number, $f_n$ equals frame number, $f_s$ equals frame size and $f_{dd}$ equals frame data cycle length.

14. The method of claim 13 further including the step of conducting an auditory brainstem response test for a test subject.

15. The method of claim 14 wherein data for the auditory brainstem response test is obtained by counting zero crossings of an internally generated, correlated sinusoid.

16. An auditory screening device, comprising:
a portable hand-held enclosure;
a signal processor housed by said enclosure;
at least one input/output interface housed by said enclosure and operatively coupled to said signal processor;
a memory module housed by said enclosure, said memory module operatively connected to said signal processor and configured to maintain at least one test subject record;
wherein said signal processor is configured to transmit and receive signals through said at least one input/output interface to conduct one or more auditory test procedures selected from a group comprising otoacoustic emission test procedures, otoreflectance test procedures, auditory brainstem response test procedures, tympanometry test procedures on a test subject; and
wherein said signal processor is configured to process otoacoustic emission signals received through said input/output interface using an offset frame overlap method to reduce uncorrelated noise present in results associated with said otoacoustic emissions test procedure.

17. The auditory screening device of claim 16 further including:
a display screen mounted to said enclosure, said display screen being operatively connected to said signal processor; and
wherein said signal processor is further configured to display results associated with a selected test procedure on said display screen.

18. The auditory screening device of claim 16 wherein said at least one input/output interface is an otoacoustic emission interface, said otoacoustic emission interface including at least one sound transducer configured to present a variety of acoustic signals to a test subject ear, and a microphone configured to receive response acoustic signals from said test subject ear.

19. The auditory screening device of claim 18 wherein said otoacoustic emission interface is further configured for otoreflectance measurements of a test subject middle ear condition.

20. The auditory screening device of claim 18 wherein said signal processor is further configured with an otoacoustic auditory emission simulator program, whereby said signal processor is configured to generate simulated $f_{dp}$ tones in response to tones generated by said sound transducer.

21. The auditory screening device of claim 16 wherein said at least one input/output interface is an auditory brainstem interface, said auditory brainstem interface including at least one sound transducer configured to present an auditory stimulus to a test subject ear, and at least one electrode configured to receive response bioelectrical signals from said test subject.

22. The auditory screening device of claim 16 wherein said at least one input/output interface is a tympanometry interface, said tympanometry interface including at least one electronic control channel, a pump operatively coupled to said electronic control channel for altering a pressure level in a test subject ear, and a pressure sensor configured to measure said pressure level in said test subject ear.

23. The auditory screening device of claim 16 wherein said signal processor is further configured, for each auditory test procedure, to transmit at least one stimulus signal though said input/output interface.

24. The auditory screening device of claim 16 further including a display device mounted to said enclosure, said display device being operatively connected to said signal processor, said display device displaying the results of said one or more selected auditory test procedures.

* * * * *

UNITED STATES PATENT AND TRADEMARK OFFICE
CERTIFICATE OF CORRECTION

PATENT NO.     : 6,974,421 B1
DATED          : December 13, 2005
INVENTOR(S)    : Elvir Causevic It is certified that error appears in the above-identified patent and that said Letters Patent is hereby corrected as shown below:

Column 9,
Line 19, replace "17" with -- 117 --.

Signed and Sealed this

Fourteenth Day of March, 2006

JON W. DUDAS
*Director of the United States Patent and Trademark Office*